United States Patent [19]
Gleich

[11] Patent Number: 5,827,512
[45] Date of Patent: *Oct. 27, 1998

[54] METHOD FOR THE TREATMENT OF BRONCHIAL ASTHMA AND LIKE HYPERSENSITIVITY DISEASES BY ADMINISTRATION OF ANIONIC POLYMERS

[75] Inventor: Gerald J. Gleich, Rochester, Minn.

[73] Assignee: Donlar Corporation, Bedford Park, Ill.

[*] Notice: The term of this patent shall not extend beyond the expiration date of Pat. No. 5,250,293.

[21] Appl. No.: 790,285

[22] Filed: Jan. 28, 1997

Related U.S. Application Data

[60] Division of Ser. No. 120,125, Sep. 10, 1993, Pat. No. 5,681,555, which is a continuation-in-part of Ser. No. 689,154, Apr. 22, 1991, Pat. No. 5,250,293.

[51] Int. Cl.⁶ .......................... A61K 31/765; A61K 38/00
[52] U.S. Cl. ...................... 424/78.05; 514/826; 514/914; 424/78.04; 424/449; 424/423
[58] Field of Search ............................ 424/78.05, 78.04, 424/78.02; 514/826, 914, 887

[56] References Cited

U.S. PATENT DOCUMENTS

| | | | |
|---|---|---|---|
| 3,074,852 | 1/1963 | Mayron | 167/82 |
| 3,202,557 | 8/1965 | Kaufman | 149/109 |
| 3,330,729 | 7/1967 | Johnson | 167/82 |
| 3,608,063 | 9/1971 | Banker | 424/22 |
| 4,021,387 | 5/1977 | Goetzl et el. . | |
| 4,226,848 | 10/1980 | Nagai et al. | 424/19 |
| 4,322,402 | 3/1982 | Ishikawa et al. | 424/78 |
| 4,623,723 | 11/1986 | Keller et al. . | |
| 4,795,436 | 1/1989 | Robinson | 424/422 |
| 4,816,449 | 3/1989 | Hahn | 514/17 |
| 4,937,232 | 6/1990 | Bell et al. | 514/26 |
| 5,000,936 | 3/1991 | Chibret | 424/43 |
| 5,036,056 | 7/1991 | Kludas | 514/54 |
| 5,145,677 | 9/1992 | Von Eichbron et al. | 424/85 |
| 5,198,350 | 3/1993 | Horisberger et al. | 435/91 |
| 5,200,177 | 4/1993 | Leung et al. | 424/85 |
| 5,250,293 | 10/1993 | Gleich . | |
| 5,324,510 | 6/1994 | Wegner et al. | 424/858 |
| 5,380,716 | 1/1995 | Conrad et al. . | |

FOREIGN PATENT DOCUMENTS 511948  6/1976  Russian Federation .

OTHER PUBLICATIONS

"Actimmune", *1993 Physician's Desk Reference Edition 47*, pp. 1078–1079 (1993).
"Anionic Polymeric Drugs", L.Guy Donaruma et al., eds., Wiley–Interscience, NY, Chapters 5 and 8, (1980).
"The Merck Index", 11th Ed., p. 1243.
Ahmed, et al., *New Engl. J of Med., 329*, 90, (1993).
Arm, J.P., et al., "The Pathobiology of Bronchial Asthma", *Advances in Immunology, 51*, 323–382, (1992).
Ayars, G.H., et al., "Injurious effect of the eosinophil peroxide–hydrogen peroxide–halide system and major basic protein on human nasal epithelium in vitro", *Am. Rev. Resp. Dis., 140*, 125–131, (1989).
Barker, R.L., et al., "Acidic polyamino acids inhibits human eosinophil granule major basic protein toxicity", *FASEB J., 4*, Abstr. 26, A1699, (1990).
Barker, R.L., et al., "Acidic polyamino acids inhibit human eosinophil granule major basic protein toxicity", *J. Clin. Invest., 88*, 798–805, (1991).

(List continued on next page.)

*Primary Examiner*—Thurman K. Page
*Attorney, Agent, or Firm*—Olson & Hierl, Ltd.

[57] ABSTRACT

A method is provided for treating a hypersensitivity disease comprising parenterally administering to a human afflicted with such a disease an amount of an anionic polymer effective to counteract the symptoms of a disease selected from the group consisting of bronchial asthma, eosinophil-associated nasal inflammation and vernal conjunctivitis, by counteracting the effect of at least one cationic toxin released by the eosinophils of said human.

19 Claims, 3 Drawing Sheets

OTHER PUBLICATIONS

Bascom, R., et al., "Major basic protein and eosinophil–derived neurotoxin concentrations in nasal–lavage fluid after antigen challenge: effect of systemic corticosteroids and relationship to eosinophil influx", *J. Allergy Clin. Immunol., 84,* 338–346, (1989).

Berge, S.M., et al., "Pharmaceuticals Salts", *J. of Pharma. Sci., 66,* 1–19, (1977).

Breslow, D.S., "Biologiaclly active synthetic anionic polymers", *Am. Chem. Soc. Symposium Series, 195,* 1–9, (1982).

Corrigan, C.J., et al., "T Cells and Eosinophils in the Pathogenesis of Asthma", *Immunology Today, 13,* 501–507, (1992).

DeAngelis, P.L., et al., "Specific recognition of sulfate esters by bindin, a sperm adhesion protein from sea urchins", *Biochim. et Biophys. Acta, 1037,* 100–105, (1990).

Dunnill, M.S., "The pathology of asthma, with special reference to changes in the bronchial mucosa", *J. Clin. Path., 13,* 27–33, (1960).

Ellis, A.G., "The Pathological Anatomy of Bronchial Asthma", *J. Med. Sci., 136,* 407–429, (1908).

Filley, W.V., et al., "Identification by immunofluorescence of eosinophil granule major basic protein in lung tissues of patients with bronchial asthma", *The Lancet, 2,* 11–16, (1982).

Frigas, E., et al., "Cytotoxic Effects of the Guinea Pig Eosinophil major basic protein on tracheal epithelium", *Lab. Invest., 42,* 35–43, (1980).

Frigas, E., "Elevated levels of the eosinophil granule major basic protein in the sputum of patients with bronchial asthma", *Mayo Clinic. Proc., 56,* 345–353, (1981).

Frigas, E., et al., "The eosinophil and the pathophysiology of asthma", *J. Allergy Clin. Immunol., 7oo7,* 527–537, (1986).

Fryer, A.D., et al., "Function of Pulmonary M2 Muscarinic Receptors in Antigen–challenged guinea pigs is restored by heparin and Poly–L–glutamate", *J. Clin. Invest., 90,* 2292–2298, (1992).

Gleich, G.J., "Current understanding of eosinophil function", *Hospital Practice, Mar. 15, 1988,* 137–160, (1988).

Gleich, G.J., et al., "Cytotoxic Properties of the Eosinophil Major Basic Protein", *J. Immunol., 123,* 2925–2927, (1979).

Gleich, G.J., "Identification of a Major Basic Protein in Guinea Pig Eosinophil Granules", *J. of Exp. Medicine, 137,* 1459–1471, (1973).

Gleich, G.L., et al., "Physiochemical and Biological Properties of the Major Basic Protein from Guinea Pig Eosinophil Granules", *J. Exp. Med., 140,* 313–332(1974),.

Gleich, G.J., "The Eosinophil and bronchial asthma: current understanding", *J. Allergy and Clin. Immunol., 85,* 422–436, (1990).

Gleich, G.J., et al., "The eosinophil as a mediator of damage to respiratory epithelium: a model for bronchial hyperreactivity", *J. Allergy Clin. Immunol., 81,* 776–781, (1988).

Gleich, G.J., et al., "The Eosinophilic Leukocyte: Structure and Function", *Adv. Immunol., 39,* 177–253, (1986).

Goetzl, E.J., et al., "Eosinophil polymorphonuclear leukocyte function in immediate hypersensitivity", *Arch. Pathol., 99,* 1–4, (1975).

Gray, P.W., et al., "Interferon–y", *Human Cytokines–Handbook for Basic and Clinical Research, Aggarwal, B. B., et al., (eds), Blackwell Scientific Publications, pp. 30–45(1992),.*

Gross, N.J., et al., "Allergy, Principles and Practice (3rd edition)", *vol. 1, E. Middleton, Jr. et al., eds. (see at p. 790) Anticholinergic Drugs,* 792–808, (1988).

Gundel, R.H., et al., "Human eosinophil major basic protein induces airway constriction and airway hyperresponsiveness in primates", *J. Clin. Invest., 87,* 1470–1473, (1991).

Gundel, R.H., et al., "Repeated antigen inhalation results in a prolonged airway eosinophilia and airway hyperresponsiveness in primates", *J. Appl. Physiol., 68,* 779–786, (1990).

Hastie, A.T., et al., "The effect of purified human eosinophil major basic protein on mammalian ciliary activity", *Am. Rev. Resp. Dis., 135,* 848–853, (1987).

Hodnett, E.M., et al., "anionic polymers and biological acitvites. Effects of some new polycarboxylic acids on the Ascitic Sarcoma 180 of Mice", *J. Med. Chem., 21,* 652–657, (1978).

Horn, B.R., et al., "total Eosinophil counts in the management of bronchial asthma", *N. Engl. J. Med., 292,* 1152–1155, (1975).

Jacoby, D.B., et al., "Human Eosinophil major basic protein is in endogenous allosteric antagonist at the inhibitory muscarinic M2 receptor", *J. Clin. Invest., 91,* 1314–1318, (1993).

Kelker, H.C., et al., "Effects of Glycosidase Treatment on the Physicochemical Properties and Biological Activity of Human Interferon–y", *J. Biol. Chem., 258, 8010–8013(1983),.*

Lane, et al., *New Engl. J. of Med., 329,* 129, (1993).

Mauser, P.J., et al., "The Effect of Anti–IL–5 on antigen––Induced airway Hyperreactivity and Pulmonary Eosinophilia in guinea Pigs", *Am. Rev. Resp. Dis., 145,* A859, (1992).

Motojima, S., et al., "Toxicity of Eosinophil cationic proteins for guinea pig tracheal epithelium in vitro", *Am. Rev. Respir. Dis., 139,* 801–805, (1989).

Ottenbrite, R.M., "Anionic Polymeric Drugs", *L.G. Donamura et al., eds., Wiley–Interscience, NY, Chapters one and two,* 1–48, (1980).

Sano, E., et al., "Constitutive Long–Term Production and Characterization of Recombinant Human Interferon Gammas from Two Different Mammalian Cells", *Cell Structure and Function, 13,* 143–159(1988),.

Trocme, S.D., et al., "Conjunctival deposition of eosinophil granule major basic protein in vernal keratoconjunctivitis and contact lens–associated giant papillary conjunctivitis", *Am. J. Opthtamol., 108,* 57–63, (1989).

Udell, I.J., et al., "Eosinophil granule major basic protein and charcot–leyden crystal protein in human tears", *Am. J. Ophthamol., 92,* 824–828, (1981).

Wallen, N., et al., "Glucocorticoids inhibit cytokine–mediated eosinophil survival", *J. Immunol., 147,* 3490–3495, (1991).

Wardlaw, A.J., et al., "Eosinophils and mast cells in bronchoalveolar lavage in subjects with mild asthma", *Am. Rev. Resp. Dis., 137,* 62–69, (1988).

Wasmoen, T.L., et al., "Biochemical and amino acid sequence analysis of human eosinophil granule major basic protein", *J. of Biol. Chem., 263,* 125459–12563, (1988).

Weller, P.F., et al., "The Human Eosinophil", *Am. J. Pathol., 100,* 793–820, (1980).

METHOD FOR THE TREATMENT OF BRONCHIAL ASTHMA AND LIKE HYPERSENSITIVITY DISEASES BY ADMINISTRATION OF ANIONIC POLYMERS

CROSS-REFERENCE TO RELATED APPLICATION

This application is a divisional of U.S. patent application Ser. No. 08/120,125, filed Sep. 10, 1993, which, in turn, is a continuation-in-part of U.S. patent application Ser. No. 07/689,154, filed Apr. 22, 1991, now U.S. Pat. No. 5,250,293.

This invention was made with the assistance of NIH under grant number AI-09728. The U.S. Government has certain rights in the invention.

BACKGROUND OF THE INVENTION

For many years, bronchial asthma was regarded as an abnormality of respiratory smooth muscle in which afflicted individuals experienced the onset of bronchospasm as a consequence of overreactivity of the bronchial smooth muscle. Later, the bronchial mast cell was thought to play a critical role in the stimulation of bronchial smooth muscle by producing leukotriene C4 (the slow-reacting substance of anaphylaxis) and histamine which cause contraction. However, over the past few years, a dramatic change in thinking regarding the pathophysiology of bronchial asthma has occurred and in this new appreciation of this disease, inflammation of the airway, particularly that caused by eosinophilic leukocytes, or "eosinophils," has been suspected.

Eosinophils are a type of leukocyte containing cytoplasmic granules that stain strongly with acidic dyes. Eosinophils have been associated with bronchial asthma since the early part of this century and they are characteristically found in large numbers in the lung tissue of patients dying of asthma (A. G. Ellis et al., *J. Med. Sci.*, 136, 407 (1908)). In the mid 1970s, it was demonstrated that the severity of bronchial asthma can be related to the number of eosinophils in the peripheral blood of the patients (B. R. Horn et al., *N. Engl. J. Med.*, 292, 1152 (1975)). Also around this time, studies of eosinophils had shown the presence of basic (cationic) granule proteins. One of the principal proteins associated with eosinophil granules, the major basic protein (MBP), was so-named because in the guinea pig it comprises more than 50% of the granule protein, is strongly basic (arginine-rich), and is proteinaceous (G. J. Gleich, *J. Exp. Med.*, 137, 1459 (1973); T. L. Wasmoen et al., *J. Biol. Chem.*, 263, 12559 (1988)). MBP is toxic to worms (helminths) and mammalian cells, and causes damage to bronchial respiratory epithelium (G. J. Gleich et al., *Adv. Immunol.*, 39, 177 (1986)). For example, direct application of MBP to respiratory epithelium in concentrations as low as 10 μg/ml (7.1×10$^{-7}$M) causes ciliostasis and epithelial damage. This damage consists of desquamation of epithelial cells into the lumen of the respiratory tract, as well as frank disruption of epithelial cells. The effects of MBP were dose-related and higher doses cause damage more quickly and to a greater extent than lower doses (E. Frigas et al., *Lab. Invest.*, 42, 35 (1980)). These effects were caused both by MBP from guinea pig eosinophils and from human eosinophils on both guinea. pig and human respiratory tissues (G. J. Gleich et al., *J. Immunol.*, 123, 2925 (1979)).

The findings that MBP caused ciliostasis, desquamation of respiratory epithelial cells, and damage to the respiratory epithelial cells are suggestive of the pathologic changes observed in bronchial asthma. In bronchial asthma, an exudate of eosinophils, normal and degenerating bronchial epithelial cells, and clumps of epithelial cells, referred to as Creola bodies, are present in the bronchial lumen. In the bronchial mucosa and submucosa, edema, separation and shedding of ciliated cells, and eosinophil infiltration are seen. Thus, the effects of the eosinophil granule MBP in vitro are similar to the pathology characteristic of bronchial asthma (M. S. Dunnill, *J. Clin. Path.*, 13, 27 (1960)).

Because of this discovery, the levels of MBP in sputum of patients with bronchial asthma were measured to determine whether they were elevated and to what degree. Levels of MBP in sputum samples from 206 patients with various respiratory diseases were measured by radioimmunoassay. In 165 of these patients, MBP was not measurable or the concentrations of MBP were less than 0.1 μg/ml. In these 165 patients, only one patient carried the diagnosis of asthma. Among 41 patients with sputum concentrations of MBP greater than 0.1 μg/ml, 28 were diagnosed as having asthma and in the remaining 13 patients, six had obstructive lung disease which is often confused with asthma. In 15 patients hospitalized for treatment of asthma, sputum MBP levels ranged from 0.5 (0.04×10$^{-6}$M) to 93 μg/ml (6.6×10$^{-6}$M) (geometric mean 7.1 μg/ml, 0.51×10$^{-6}$M). Further, the levels of sputum MBP in these 15 patients declined during therapy with glucocorticoids (E. Frigas et al., *Mayo Clinic. Proc.*, 56, 345 (1981)). These results indicated that MBP levels in the toxic range were present in the sputum of patients with asthma, that levels of sputum MBP were highest in acutely ill patients, and that sputum MBP levels decline after steroid therapy.

The possibility that MBP directly causes damage to bronchial epithelium was tested utilizing immunofluorescence localization of MBP in lung tissues of patients dying of asthma (W. Filley et al., *Lancet*, 2, 11 (1982)). These results showed that the patients dying of asthma had the classical pathologic features of bronchial asthma with a thickened basement membrane zone, goblet cell hyperplasia, and peribronchial inflammatory infiltrates with eosinophils in the lamina propria. Examination of these same sections by immunofluorescence to localize MBP, revealed MBP deposition onto damaged bronchial epithelium. These results demonstrate that MBP was released from the eosinophil and was present in tissues at the site of damage.

Subsequent studies extended these observations showing that not only MBP, but two of the other cationic eosinophil granule proteins, namely eosinophil peroxidase (EPO) and eosinophil cationic protein (ECP), have the capacity to damage bronchial epithelium (S. Motojima et al., *Am. Rev. Respir. Dis.*, 139, 801 (1989)). Analyses of the effect of MBP on respiratory epithelium showed that although MBP reduced the frequency of ciliary beating, its predominant effect was to reduce the number of beating ciliated cells. The effect of MBP in causing cessation of ciliary beating was seen in respiratory epithelial cells in the epithelium itself as well as in axonemes (the contractile elements of the cilia)(A. T. Hastie et al., *Am. Rev. Resp. Dis.*, 135, 845 (1987)).

One of the signal abnormalities in bronchial asthma is bronchial hyperreactivity. Bronchial hyperreactivity is manifested in patients as a marked irritability of the respiratory tract to nonspecific stimuli including cold air, dust, and, in the laboratory, to inhaled methacholine. Indeed, this hyperreactivity is a diagnostic criterion for asthma (N. J. Gross et al., in *Allergy, Principles and Practice*, Vol. I., E. Middleton, Jr. et al., eds. (1988) at page 790). Analyses of MBP in the lung secretions of patients with asthma (obtained by lavage of the bronchi and alveoli) showed that MBP levels in lung fluids are correlated with bronchial hyperreactivity (A. J. Wardlaw et al., *Am. Rev. Resp. Dis.*, 137, 62 (1988)). In cynomolgus monkeys, provocation of inflammation rich in eosinophils was associated with an increase in bronchial hyperreactivity and with the presence of MBP in lung secretions; both the numbers of eosinophils and the MBP concentration were significantly correlated with bronchial hyperreactivity to methacholine (R. H. Gundel et al.,*J. Appl. Physiol.*, 68 779 (1990)).

The information discussed above pertains to bronchial asthma and the role of toxic eosinophil granule proteins exemplified by MBP in the pathophysiology of bronchial asthma. Evidence exists that these toxic proteins also contribute to the pathogenesis of diseases associated with eosinophil infiltration in the upper respiratory tract. For example, G. H. Ayars et al. in *Am. Rev. Resp. Dis.*, 140, 125 (1989), have reported that MBP is toxic to respiratory epithelium from the nose and the paranasal sinuses and R. Bascom et al., in *J. Allergy Clin. Immunol.*, 84, 338 (1989) found that elevated MBP concentrations are present in nasal fluids following experimental hay fever. MBP is deposited on respiratory epithelium of the upper airway in association with damage to the epithelium. Therefore, toxic eosinophil granule proteins may cause disease of the upper airway in the same manner as they likely do in the lower airway in the case of bronchial asthma.

Finally, I. J. Udell et al., in *Am. J. Ophthamol.*, 92, 824 (1981) reported that MBP is elevated in tears of patients with vernal conjunctivitis, a form of allergic inflammation of the eye, and S. D. Trocme et al., in *Am. J. Ophthamol.*, 108, 57 (1989) found that MBP is deposited into inflamed conjunctiva of such patients. Thus, evidence exists that MBP may act as a toxin to the conjunctiva.

Therefore, a need exists for a therapeutic method to treat hypersensitivity diseases, such as bronchial asthma, which are caused by, or aggravated by, toxic proteins released by eosinophils.

SUMMARY OF THE INVENTION

The present invention provides a method for treating bronchial asthma, as well as other hypersensitivity diseases, comprising administering to a human afflicted with such a disease, an amount of a pharmaceutically acceptable salt of an anionic polymer, such as the salt form of a polymeric organic carboxylic acid, in combination with a pharmaceutically acceptable carrier, wherein said amount is effective to counteract the symptoms of the bronchial asthma or other disease. It is believed that the anionic polymer counteracts the effect of at least one of the cationic toxins released by the eosinophils of the human. A preferred method of administering the anionic polymer is parenterally, as by injection, infusion, topical application or inhalation. Thus, the present method provides a therapy for bronchial asthma in the lung, eosinophil-associated intranasal inflammation, including inflammation of the paranasal sinuses, and eosinophil-associated inflammation of the eye, such as vernal conjunctivitis. Preferred salts of polymeric organic carboxylic acids or "polycarboxylates" include the acid salts of polyamino acids, also referred to as "polyamino acid salts."

The present method is believed to involve counteracting or preventing the symptomologies caused by toxic cationic eosinophil granule proteins by the parenteral administration of polyanions to the afflicted or susceptible human. For example, the present invention provides a therapy for bronchial asthma and the other hypersensitivity diseases of the respiratory tract, by intravenous injection or infusion of an anionic polymer, which is preferably a polyamino acid salt. The polyamino acid salt in turn is able to neutralize the toxic effects of eosinophil granule proteins in situ, including MBP, ECP and/or EPO, on respiratory epithelium. Topical administration of polyamino acid salts, e.g., in eyedrops, can relieve the symptoms of conditions due to eosinophil-associated inflammation of the eye, such as vernal conjunctivitis.

The present invention also provides a unit dosage form comprising an amount of a polyamino acid salt effective to treat bronchial asthma in combination with a pharmaceutically acceptable liquid carrier, such as the aqueous carriers (or vehicles) discussed hereinbelow.

The present invention is based upon discoveries that MBP is a toxin to respiratory epithelium, and mimicks the pathologic changes due to asthma, that MBP levels are present in the sputum in the range of those causing toxicity in vitro, and that MBP can be localized by immunohistology onto damaged bronchial epithelium in patients with asthma.

These observations prompted experiments to determine whether polyamino acid salts, such as the sodium salts of polyaspartic acid and polyglutamic acid, might be effective to neutralize the toxic activity of cationic MBP on cells and respiratory epithelium. These studies showed that the salts of various polymers of glutamic acid ranging from 13,600 daltons to 78,000 daltons, first, did not cause toxicity to cells in vitro and, second, were powerful inhibitors of the toxic effects of MBP at doses in the nanomolar range. Similarly, the toxic effects of ECP on cells was also inhibited by the sodium salt of polyglutamic acid. Furthermore, the toxicity of MBP to respiratory epithelium was totally inhibited by sodium polyglutamate.

Tests of the effect of the polyglutamic acid salt on the increase in respiratory resistance (bronchospasm) due to MBP administration to cynomolgus monkeys showed that sodium polyglutamate blocked the MBP-induced increase in respiratory system resistance (Rrs). Similarly, sodium polyglutamate pretreatment inhibited the MBP-induced increase in airway responsiveness. Finally, the polyglutamic acid salt at a concentration of $1 \times 10^{-5}$M, which is twice the highest concentration utilized in analyses of the toxicity of MBP to cells, had no effect on blood clotting. Even at a concentration of $10^{-4}$M, the sodium salt of polyglutamic acid (77,800 daltons) caused only a slight prolongation of blood clotting.

Figure 1:
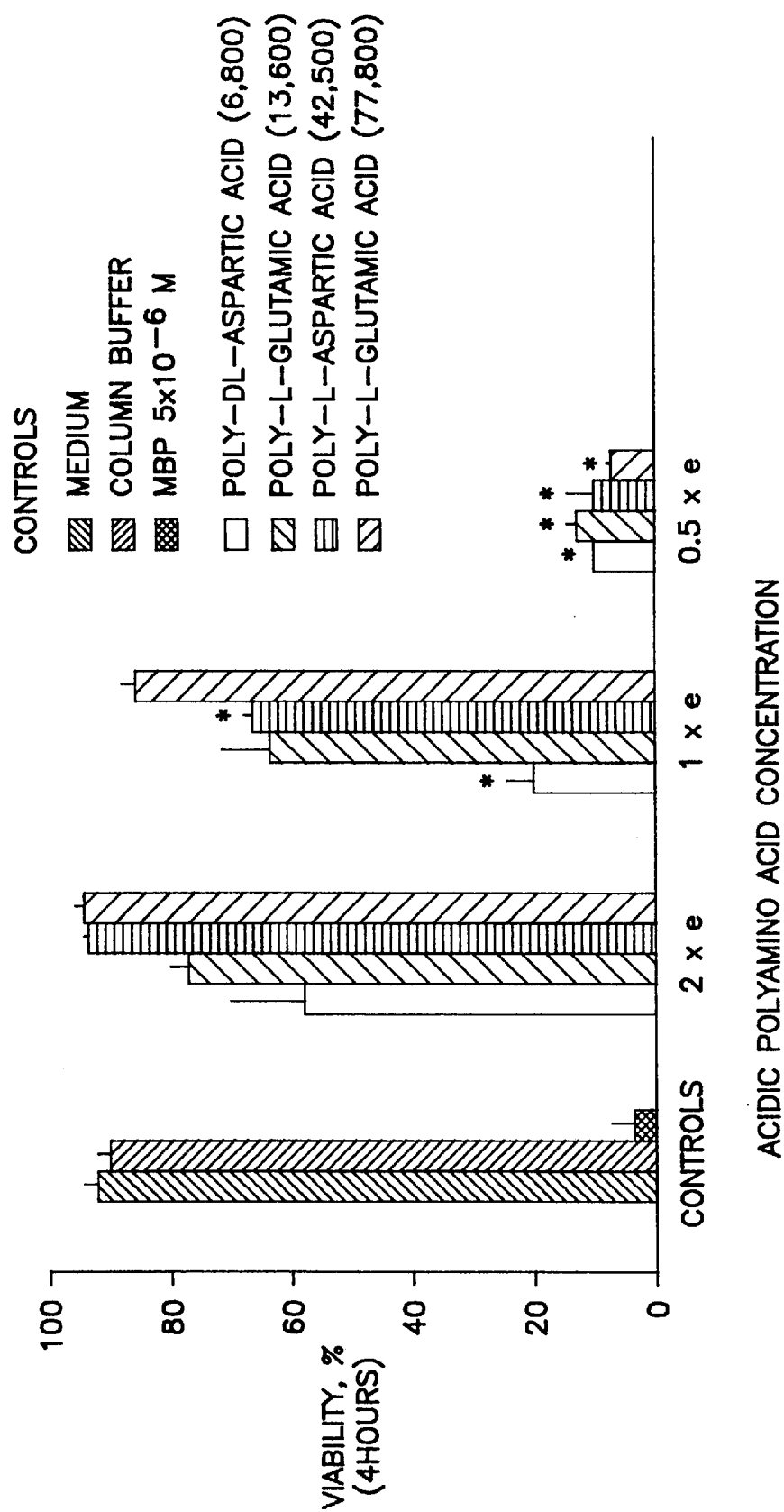
FIG. 1 is a graphic depiction of the acidic polyamino acid salt inhibition of MBP toxicity to K562 cells at 2, 1 and 0.5 times the acidic polyamino acid ("aa") concentration necessary to balance the cationic charge of MBP at $5.0 \times 10^{-6}$M. Values are mean percent±1SD of 1 experiment consisting of duplicate wells. (*) indicates p<0.01 for values tested against appropriate controls using Student's t-test.

indicates p<0.001 for values tested against saline control using Student's t-test.

DETAILED DESCRIPTION OF THE INVENTION

Anionic Polyamino Acids

A wide variety of nontoxic anionic polymers, including the preferred polyamino acid salts are effective when administered in accord with the present method. Of these salts, the alkali metal salts (e.g., $Na^+$, $K^+$, $Li^+$), ammonium or amine salts of homo- or hetero-anionic (random copolymers) polyamino acids such as polyglutamic acid, polyaspartic acid, poly(aspartic acid, glutamic acid) and the like are preferred, and may include optically active or racemic peptidyl subunits. For example, the sodium salt of poly-($\alpha$, $\beta$)-DL-aspartic acid (m.w. 2,000–10,000) is available from Sigma Chem. Co., as is the sodium salt of poly-L-aspartic acid (m.w. 5,000–15,000 and 15,000–50,000). The sodium salt of poly-D-glutamic acid is available in a number of m.w. ranges (2,000–15,000, 15 kD–50 kD, 50 kD–100 kD) as is the sodium salt of poly-L-glutamic acid (2–15 kD, 15–50 kD, 50–100 kD).

Other nontoxic anionic polymers and their salts can also be used effectively in the present method, including polycarboxylates, polysulfates and polyphosphates. Preferably, the molecular weight of these polymers is greater than 1,000 daltons, preferably, it is greater than about 5000 daltons, i.e., about 10,000–100,000 daltons.

Preferred polycarboxylic acids include those nontoxic acidic polymers which can adhere to mucus membranes and which can thereby exhibit prolonged bioactivity at the sites of MBP activity. These include solid water-swellable, preferably cross-linked carboxy-functional polymers and the salts thereof. The polymers contain (a) a plurality of repeating units of which at least about 80 percent contain at least one carboxyl functionality, and can comprise (b) about 0.05 to about 1.5 percent cross-linking agent, with the percentages being based upon the weights of unpolymerized repeating unit and cross-linking agent, respectively. In more preferred practice, at least about 90 percent of the repeating units contain at least one carboxyl functionality, and in still more preferred practice, at least 95 percent of those repeating units contain at least one carboxyl functionality. Most preferably, the polymer is a reaction product of the polymerization of only a carboxyl-functional monomer and, optionally, the cross-linking agent, although co-monomers, such as ethylene and other alkenes, can be used in minor amounts.

As noted previously, at least about 80 percent of the repeating units of the bioadhesive contain at least one carboxyl functionality. Exemplary monomers that provide these repeating units are monoethylenically unsaturated and include acrylic acid, methacrylic acid, fumaric acid, maleic acid, maleic anhydride which may be hydrolyzed into its acid form during or after polymerization, itaconic acid, crotonic acid, and the like. Each of these acids may be used alone or in combination with other such acids or with one or more pharmaceutically acceptable salts of those acids. Acrylic acid, maleic anhydride and methacrylic acid are particularly preferred monomers for providing the repeating units of the bioadhesive polymer.

The polyanions of this invention are optionally cross-linked by known cross-linking agents. Exemplary of useful cross-linking agents are divinylether, divinylbenzene, N,N-diallylacrylamide, 3,4-dihydroxy-1,5-hexadiene, 2,5-dimethyl-1,5-hexadiene, polyalkenyl polyethers (Carbopol® 934) and the like.

The amount of cross-linking of the polyacid is of some import. When less than about 0.05 weight percent of an appropriate cross-linking agent is present, the polycarboxylate tends to become water-soluble, or water-dispersible. When greater than about 1 percent cross-linking agent is present, the water-swellability of the polycarboxylate begins to decrease appreciably. For exemplary materials of both types, see U.S. Pat. Nos. 4,795,436, 3,074,852, 3,330,729, 3,608,063, 4,226,848 and 3,202,577.

One commercially available cross-linked polyacrylic acid useful in the present invention is polycarbophil (A.H. Robbins Co.). Other useful organic polymers containing carboxylic acid or carboxylate groups include pyran copolymer, chlorite oxidized oxyamylose, the copolymer of acrylic acid and allyl sucrose (Carbopol), carboxymethylcellulose, starch glycolic acid, and other polymeric derivatives of acrylic acid such as poly(acrylic acid-isobutyl vinyl ether and the copolymers of acrylic acid and dimethylaminoethylacrylate).

Useful polysulfates include poly[vinylsulfate], chondroitin sulfate, dextran sulfate, polyethylene sulfonate and polystyrene sulfonic acid. Useful polyphosphates include dextran phosphate and certain polynucleotides, such as polyinosinic acid, polycyticyclic acid, polyxenyl phosphate. For other polyanions that may be useful in the practice of the invention, see *Anionic Polymeric Drugs*, L. G. Donaruma et al., eds. Wiley-Interscience (1980).

Administration and Dosages

While it is possible that, for use in therapy, the anionic polymer salts may be administered as the pure chemicals, as by inhalation of a fine powder via an insufflator, it is preferable to present the active ingredient as a pharmaceutical formulation. The invention thus further provides a pharmaceutical formulation comprising one or more anionic polymer salts, or a pharmaceutically acceptable derivative thereof, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for parenteral administration by injection, infusion, inhalation or insufflation or for nasal, or topical (including buccal and sub-lingual) administration. The formulations may, where appropriate, be conveniently presented in discrete dosage units and may be prepared by any of the methods well known in the art of pharmacy. All methods include the step of bringing into association the active compound with liquid carriers, such as isotonic saline or PBS, or finely divided solid carriers or both.

It is well-known that MBP is found within the submucosa of the bronchi during asthmatic attacks, and here the MBP presumably triggers bronchial constriction and the sensitivity of the bronchi to inhaled methacholine. It is also known that pharmaceutical compositions administered intravenously can reach the submucosa and reverse bronchospasm, for example, intravenous isoproterenol is utilized to treat bronchial asthma. Fryer et al. have shown in the guinea pig that parenterally administered polyglutamate diffuses to the muscarinic receptors in the epithelium (A. D. Fryer et al., *J. Clin. Invest.*, 90, 2292 (1992)). MBP has been shown to be an endogenous allosteric inhibitor of the M2 receptor (D. B. Jacoby et al., *J. Clin. Invest.*, 91, 1314 (1993)).

Pharmaceutical formulations intended for parenteral administration by intravenous injection or infusion or by enteral injection or infusion are particularly useful in cases of severe status asthmaticus, in which the patient may be comatose or unable to inhale deeply enough to draw the polyanion into the lung by inhalation. In other cases, the patient may be too young or mentally impaired so that the patient cannot follow verbal instructions on inhalation. Additionally, areas of the lung may be blocked by mucus plugs or inaccessible to a drug administered via inhalation.

For administration to the respiratory tract by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer (Wintrop) and the Medihaler (Riker).

Drops, such as eye drops, may be formulated with an aqueous or non-aqueous base also comprising one or more dispersing agents, solubilizing agents or suspending agents. Liquid sprays are conveniently delivered from pressurized packs.

For topical administration to the eye or epidermis, the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

When desired, the above-described formulations adapted to give sustained release of the active ingredient may be employed, e.g., by combination with certain hydrophilic polymer matrices. Such formulations can be used for the delivery of the active ingredient transdermally, as from a patch adhered to the skin, or by iontophoresis.

The pharmaceutical compositions according to the invention may also contain other active ingredients such as antimicrobial agents, or preservatives.

The compounds of the invention may also be used in combination with other therapeutic agents, for example, other broncodilators or anti-inflammatory agents.

It will be further appreciated that the amount of a compound of the invention required for use in treatment will vary not only with the particular compound selected but also with the route of administration, the nature of the condition being treated and the age and condition of the patient and will be ultimately at the discretion of the attendant physician or veterinarian. In general, however, a suitable unit dose for counteracting respiratory tract symptomology will deliver from about 0.05 to about 5 mg/kg, e.g., from about 1 to about 2.5 mg/kg of body weight per day. The total dose of polyanion administered, however, may be less critical than the concentration achieved in situ in comparison to the known highest concentration of MBP in the affected physiological fluid. For example, the concentration of MBP in sputum can be as high as $7.1 \times 10^{-6}$M. In this case, a solution of polyglutamic acid, 50 mg/ml at $6.4 \times 10^{-4}$M for the 77.8 kD polyment, would provide a 90-fold greater concentration than the highest sputum MBP measured in an asthma patient.

The desired dose may conveniently be presented in a single dose or as divided doses administered at appropriate intervals, for example, as two, three, four or more sub-doses per day. The sub-dose itself may be further divided, e.g. into a number of discrete loosely spaced administrations; such as multiple inhalations from an insufflator, multiple injections, or by application of a plurality of drops into the eye.

The invention will be further described by reference to the following detailed Example.

EXAMPLE 1

Neutralization of the Effects of MBP by Polyamino Acids

A. Materials and Methods

1. Reagents and Media

Sodium salts of amino acids, sodium salts of amino acid polymers (Table I), RPMI-1640 medium containing L-glutamine and methacholine were purchased from Sigma Chemical Co. (St. Louis, Mo.). Defined calf serum (DCS) was obtained from Hyclone Laboratories, Inc. (Logan, Utah). Ketamine (Ketaset) and xylazine (Rompun) were purchased from Bristol Laboratories (Evansville, Ind.) and Miles Inc. (West Haven, Conn.), respectively.

TABLE I

Properties of Amino Acid Salts

| | Mol wt | Degree of polymerization* | Charge (e) at pH 7.0[‡] | Concentration for balanced charge[#] |
|---|---|---|---|---|
| L-aspartic acid (A-0651)[⁻] | 155 | 1 | −1.1 | (a)$7.5 \times 10^{-5}$M |
| L-glutamic acid salt (G-1626) | 169 | 1 | −1.1 | (a)$7.5 \times 10^{-5}$M |
| Poly-(α,β)-DL-aspartic acid (P-3418) | 6,800 | 50 | −50.1 | (a)$1.6 \times 10^{-6}$M |
| Poly (aspartic acid, glutamic acid) 1:1 (P-1408) | 9,000 | 60 | −60.0 | (a)$1.4 \times 10^{-6}$M |

TABLE I-continued

Properties of Amino Acid Salts

|  | Mol wt | Degree of polymerization* | Charge (e) at pH 7.0‡ | Concentration for balanced charge# |
|---|---|---|---|---|
| Poly-L-aspartic acid (P-5387) | 11,500 | 84 | −84.0 | (a)9.7 × 10⁻⁷M |
| Poly-L-glutamic acid (P-4636) | 13,600 | 90 | −89.9 | (a)9.1 × 10⁻⁷M |
|  |  |  |  | (b)3.3 × 10⁻⁶M |
|  |  |  |  | (c)8.1 × 10⁻⁷M |
| Polyglutamic acid (P-4761) | 36,240 | 240 | −239.0 | (a)3.4 × 10⁻⁷M |
| Poly-D-glutamic acid (P-4033) | 41,000 | 272 | −271.0 | (a)3.0 × 10⁻⁷M |
| Poly-L-aspartic acid (P-6762) | 42,500 | 310 | −310.0 | (a)2.6 × 10⁻⁷M |
| Poly-D-glutamic acid (P-4637) | 66,000 | 437 | −436.0 | (a)1.9 × 10⁻⁷M |
| Poly-L-glutamic acid (P-4886) | 77,800 | 515 | −514.0 | (a)1.6 × 10⁻⁷M |
|  |  |  |  | (b)5.9 × 10⁻⁷M |
|  |  |  |  | (c)1.4 × 10⁻⁷M |
| Poly-L-asparagine (P-8137) | 10,400 | 91 | −0.1 |  |
| Native MBP | 13,801 | 117 | 16.3 |  |
| Poly-L-arginine hydrochloride (P-4663) | 12,000 | 62 | 60.9 |  |
| ECP | 16,000 | 133 | 14.5 |  |

*Degree of polymerization indicates number of amino acid (aa) residues per molecule.
‡Charge (e) calculated by Titrate program (DNAstar., Inc., Madison, WI).
Concentration of acidic aa necessary to balance charge of cationic (a) MBP at 5 × 10⁻⁶M, (b) poly-L-arginine hydrochloride at 5 × 10⁻⁶M, or (c) ECP at 5 × 10⁻⁶M.
°All acids used were purchased as sodium salts unless otherwise noted; Sigma product code appears in parentheses after the product name.

2. Purification of MBP and ECP

Eosinophils from patients with the hyper-eosinophilic syndrome were obtained and after thorough washing to remove plasma proteins, erythrocytes were lysed by exposure to hypotonic saline. After additional washing, the resulting preparations of eosinophils (greater than 85% pure) were lysed by exposure to 0.25M sucrose and mechanical agitation, as well as addition of heparin (needed on some occasions to induce eosinophil lysis). The broken cell preparations were centrifuged to remove cell debris and unbroken cells, and granule-containing supernatants were pooled and were centrifuged. Granule pellets were solubilized in 0.01M HCl (final pH 3.0) with brief sonication and centrifuged at 40,000×g for 5 minutes. The supernatant was fractionated at 4° C. on a Sephadex G-50 column equilibrated with 0.025M sodium acetate buffer (pH 4.2) containing 0.15M NaCl (column buffer). Fractions from the second protein peak containing ECP were pooled, dialyzed, lyophilized and further purified as described below. Fractions from the third protein peak, containing only eosinophil major basic protein (MBP), were pooled. MBP concentrations were determined by absorbance at 277 nm using the extinction coefficient $E_1\ _{cm}^{1\%}$=26.3.

Eosinophil cationic protein (ECP) was further purified by affinity chromatography on a heparin Sepharose CL-6B column equilibrated with phosphate buffered saline (PBS) at pH 7.4. Fractions containing ECP eluted from the heparin-Sepharose at high salt concentrations (0.15M–1.5M NaCl gradient used) and were pooled, dialyzed against PBS and concentrated by lyophilization. ECP concentrations were determined by absorbance at 277 nm using the extinction coefficient $E_1\ _{cm}^{1\%}$=15.6.

3. Cytotoxicity and Inhibition of Toxicity Assays

K562 cell cultures (ATCC CCL 243) were maintained in the tissue culture medium RPMI-1640 supplemented with L-glutamine and 10% defined calf serum (DCS) by twice weekly passage. Two days prior to assay, cells were resuspended at 4×10⁴ cells/ml of fresh RPMI-1640 with 10% DCS, pH 7.4, in 50 ml flasks. By the day of assay, cell numbers had reached 1.5–2.0×10⁵/ml. These cells were washed three times in RPMI-1640 without DCS, resuspended to 5×10⁵ cells/ml and duplicate 100 μl aliquots were dispensed to flat-bottomed 96-well microtiter plates. Fifty microliters of various concentrations of amino acid salts dissolved in RPMI-1640 or RPMI-1640 alone were added followed at the appropriate time by 50 μl of MBP in column buffer, poly-L-arginine in RPMI-1640, ECP in RPMI-1640 or appropriate controls. MBP, poly-L-arginine and ECP were used at a final concentration of 5×10⁻⁶M. Cells were incubated for 4 hr at 37° C. in a 5% $CO_2$ atmosphere in a humidified chamber. Cell viability was determined by microscopic observation using trypan blue exclusion, and mean percent viability±1SD of duplicates from one or more experiments was calculated. Differences in viability between nontoxic controls and test concentrations were evaluated statistically using Student's t-test. After initial experiments using several polyamino acid salts, the sodium salt of poly-L-glutamic acid (13,600 mol wt) and the sodium salt of poly-L-glutamic acid (77,800 mol wt), the lowest and highest molecular weight polyglutamic acid homopolymers available, were used as typical representatives of this class of compounds.

4. Guinea Pig Tracheal Ring Assay

Tracheal rings were prepared from Hartley guinea pigs (Mayo Institute Hills Farm, Rochester, Minn.). Immediately following $CO_2$ euthanasia, tracheas were removed and placed in RPMI-1640. Adherent connective tissue was trimmed and each trachea was cut transversely into a series of 1 mm thick rings using a slicing device. After overnight equilibration, each ring was carefully examined to determine that the mucosa was intact and actively beating cilia were present. Rings with damaged mucosa were not used for experimentation.

For testing, rings were transferred to 96-well microtiter plates containing 100 μl RPMI-1640/well. Fifty microliters of the sodium salts of polyamino acids at a final concentration of 1.4×10⁻⁵M or RPMI-1640 alone were added to the wells, followed within 5 minutes by addition of 50 μl of MBP at a final concentration of 1.4×10⁻⁵M, or of controls (column buffer or RPMI-1640). An observer, unaware of the substance or combination being tested, examined the ring cultures at 24 hr and 48 hr, using an inverted microscope. After final observations, specimens were fixed in 10% buffered formalin, embedded in paraffin, sectioned and stained with hematoxylin and eosin.

5. Criteria for Damage to Tracheal Epithelium

Ciliostasis was used to describe the complete cessation of ciliary motion throughout the entire tracheal ring; "normal" tracheal rings had active, intact ciliary epithelium. At the time intervals when damage was assessed, ciliostasis was almost always accompanied by partial or complete exfoliation or "stripping" of the ciliated epithelial cells from the basement membrane of the mucosa with precipitates of MBP on or around the cells.

6. Airway Hyperresponsiveness and Inhibition of Hyperresponsiveness Assays a) Animals. The animals used in this study were wild-caught adult male cynomolgus monkeys (*Macaca fascicularis*) weighing 3.5 to 7.5 kg. Each animal was housed individually in a specially designed open mesh cage and provided with food twice daily and water ad libitum. Animals were fasted for approximately 18 hr prior to study.

b) Study Protocol. Each animal was anesthetized with an intramuscular injection of ketamine (4 mg/kg) and xylazine (1 mg/kg), intubated with a cuffed endotracheal tube and seated in an upright position in a specially designed support chair. Ketamine (4 mg/kg, i.m.) was used to supplement anesthesia when needed. The baseline respiratory system resistance (Rrs) was monitored for 15 minutes followed by methacholine dose-response determinations. The bronchoconstrictor response to inhaled methacholine was used to determine airway responsiveness by the methodology C. D. Wegner et al., *Respir. Physiol.*, 55, 47 (1984) and R. H. Gundel et al., *J. Appl. Physiol.*, 68, 779 (1990).

After completion of the methacholine dose-response, each animal received an aerosol treatment of either vehicle or polyglutamic acid salt (P-4886, 61,200 mol wt). Rrs was monitored for an additional 10 minutes after which each animal received an intratracheal injection of native MBP. Rrs was then monitored for one hour post-instillation after which the animals were allowed to recover from anesthesia. At 2 hr postinstillation, each animal was anesthetized (ketamine/xylazine), intubated and methacholine dose-response determinations were performed. The study was designed so that the sodium polyglutamate treatment experiments were bracketed by control (vehicle) treatment studies to ensure no change in MBP-induced effects over time.

c) Intratracheal MBP Instillation. Native MBP was diluted in pH 4.3 0.025M sodium acetate buffer containing 0.15M NaCl to a concentration of 200 $\mu$g/ml immediately prior to instillation. A total of 5 ml (1 mg MBP) was slowly infused directly into the trachea through the endotracheal tube via a 20 cm long piece of polyethylene 240 tubing attached to a 5 ml syringe. As control fluids, PBS and column buffer were tested and produced no effect on Rrs or methacholine sensitivity.

d) Rrs Measurements. Respiratory system impedance (Zrs) was measured as reported by C. D. Wegner et al., cited above, by discrete frequency sinusoidal forced oscillations superimposed on tidal breathing. The frequency range was computed to provide a single value representation of respiratory system resistance (Rrs).

e) Aerosol Delivery System. Aerosol inhalation treatments of vehicle or polyglutamic acid salt were administered by intermittent positive pressure breathing with a Bird Mark 7A respirator and micronebulizer (Model 8158, Bird Corporation, Palm Springs, Calif.). Each treatment consisted of 15 breaths per minute (maximum inspiratory pressure 20 cm $H_2O$) for 6 minutes. Sodium polyglutamate was dissolved in PBS at a concentration of 25 mg/ml just prior to use. Aerosol treatment delivered approximately 1.5 mg of polyglutamic acid salt to the lungs.

f) Methacholine Dose-Response Determinations. Bronchial responsiveness was assessed by performing cumulative methacholine dose-response determinations (R. H. Gundel et al., J. Appl. Physiol., 68, 779 (1990)). After an initial aerosol challenge with vehicle (PBS), increasing concentrations of methacholine were administered until increases in Rrs of 100 to 200 percent were obtained. Aerosol challenges were separated by 5–8 minutes or until Rrs returned to baseline values. Linear interpolation on a logarithmic scale was used to estimate the dose of methacholine at which a 100 percent increase in Rrs would have occurred (methacholine $PC_{100}$).

7. Inhibition of Blood Clotting

To determine whether polyamino acid salts inhibit blood clotting, stock concentrations of heparin, poly-L-glutamic acid sodium salt (13,600 mol wt) and poly-L-glutamic acid sodium salt (77,800 mol wt) were added to 500 $\mu$l whole blood from a normal human volunteer to final concentrations of $10^{-4}$M to $10^{-6}$M in 10×75 mm glass tubes and mixed. PBS and column buffer were used as controls. The tubes were checked at one-minute intervals and clotting time for each sample was recorded. After 30 minutes, samples were checked every 30 minutes to a maximum of 15 hr.

B. Results

1. Inhibition of MBP Toxicity to K562 Cells by Acidic Polyamino Acid Salts

Various polyglutamic and polyaspartic acid salts were added to K562 cells followed by addition of MBP and cell viability was determined after 4 hr. The results of these experiments are summarized on Table II, below.

TABLE II

Inhibition of MBP Toxicity by Acidic Amino Acid Salts

Percent Viability of K562 Cells*

| | | | Native MBP (5 × $10^{-6}$M) added to aa concentration | | | | |
|---|---|---|---|---|---|---|---|
| | Mol wt | Controls‡ | 1 × $10^{-3}$M | 5 × $10^{-6}$M | 1 × $10^{-6}$M | 5 × $10^{-7}$M | 1 × $10^{-7}$M |
| L-aspartic acid** | 155 | 98.5 ± 0.2 | 3.4 ± 4.7# | ND | ND | ND | ND |
| L-glutamic acid | 169 | 98.8 ± 0.2 | 0.0 ± 0.0# | ND | ND | ND | ND |
| Poly-($\alpha,\beta$)-DL-aspartic acid | 6,800 | 97.0 ± 2.7 | ND | 90.1 ± 6.7~ | 1.6 ± 1.5 | 6.0 ± 3.9# | 2.9 ± 0.4# |
| Poly(aspartic acid, glutamic acid) 1:1 | 9,000 | 98.4 ± 1.4 | ND | 95.5 ± 0.9 | 22.0 ± 19.7# | 4.9 ± 2.3# | 0.0 ± 0.0# |

TABLE II-continued

Inhibition of MBP Toxicity by Acidic Amino Acid Salts

Percent Viability of K562 Cells*

| | | | Native MBP ($5 \times 10^{-6}$M) added to aa concentration | | | | |
|---|---|---|---|---|---|---|---|
| | Mol wt | Controls‡ | $1 \times 10^{-3}$M | $5 \times 10^{-6}$M | $1 \times 10^{-6}$M | $5 \times 10^{-7}$M | $1 \times 10^{-7}$M |
| Poly-L-aspartic acid | 11,500 | 98.0 ± 2.4 | ND | 87.5 ± 7.9 | <u>84.3 ± 1.6</u># | 22.7 ± 7.2# | 2.7 ± 3.8# |
| Poly-L-glutamic acid | 13,600 | 98.9 ± 1.0 | ND | 89.5 ± 2.0 | <u>72.9 ± 0.7</u># | 4.9 ± 5.9# | 0.0 ± 0.0# |
| Poly-L-glutamic acid | 36,240 | 94.7 ± 2.6 | ND | 96.2 ± 6.5 | 96.9 ± 1.8 | <u>67.5 ± 20.4</u> | 1.3 ± 1.8# |
| Poly-D-glutamic acid | 41,000 | 100.0 ± 0.0 | ND | 98.0 ± 1.8 | 99.0 ± 1.7 | <u>96.2 ± 1.4</u> | 11.2 ± 0.9# |
| Poly-L-aspartic acid | 42,500 | 97.4 ± 2.3 | ND | 100.0 ± 0.0 | 99.4 ± 0.9 | <u>100.0 ± 0.0</u> | 8.7 ± 1.4# |
| Poly-D-glutamic acid | 66,000 | 93.4 ± 6.1 | ND | 96.4 ± 1.7 | 97.3 ± 1.0 | <u>90.6 ± 3.4</u> | 0.0 ± 0.0# |
| Poly-L-glutamic acid | 77,800 | 95.1 ± 3.8 | ND | 93.9 ± 8.0 | 95.5 ± 6.4 | <u>95.4 ± 3.2</u> | 2.6 ± 3.5# |
| Poly-L-asparagine | 10,400 | 85.3 ± 5.1 | ND | 5.9 ± 9.5# | 1.2 ± 2.1# | 0.0 ± 0.0 | 0.0 ± 0.0# |
| Native MBP | 13,801 | 1.0 ± 3.2 | | | | | |
| Column buffer | | 96.7 ± 1.6 | | | | | |
| Medium | | 96.5 ± 3.7 | | | | | |

**All acids were used as sodium salts.
*Values are mean percent viability ± 1 SD of 1–3 4 hr experiments, each consisting of duplicate wells.
‡Controls consist of aa, acidic poly aa, poly-L-asparagine, native MBP, column buffer or medium tested alone. All controls at $5 \times 10^{-6}$M except L-aspartic and L-glutamic acid monomers which were tested at $1 \times 10^{-3}$M.
Indicates $p < 0.001$ for values tested against appropriate nontoxic aa control using Student's t-test; MBP added within five minutes after addition of acidic aa.
¨Values underlined are from acidic polyamino acid test concentrations closest to but not less than concentration for balanced charge (Table I) for a particular acidic polyamino acid.

The polyamino acid salts ranged from 6,800 to 77,800 in mol wt (Table I) and were tested at concentrations from $1 \times 10^{-7}$M to $5 \times 10^{-6}$M for their ability to inhibit MBP toxicity at $5 \times 10^{-6}$M. As shown on Table II, all of the polyamino acid salts inhibited MBP toxicity at equimolar MBP concentrations. This inhibition was related to the acidic or anionic nature of the polymers because poly-L-asparagine at $5 \times 10^{-6}$M did not inhibit MBP toxicity. Also, some degree of polymerization was necessary for this effect because amino acid monomers did not inhibit MBP toxicity. The amino acid salts, themselves, were not toxic to the K562 cells at the concentrations tested.

As the concentration of the polyamino acid salt was lowered below that of MBP, inhibition of MBP toxicity to the K562 cells was reduced (Table II). This reduction was not due to the type of amino acid present (glutamic acid versus aspartic acid, or D versus L isomers) but was dependent upon the molecular weight and thus the degree of polymerization of the polyamino acid. Because the degree of polymerization directly affects the total charge (e) of the polymer salts, a comparison between the polyamino acid salt concentrations necessary to balance the e of MBP at $5 \times 10^{-6}$M and the reduction in polyamino acid salt inhibition of MBP toxicity to K562 cells was made (Tables I and II).

At polymer salt concentrations greater than or equal to those necessary to balance the cationic charge of MBP, only the sodium salt of poly-L-aspartic acid (11,500 mol wt) and the sodium salt of poly-L-glutamic acid (13,600 mol wt), both at $1 \times 10^{-6}$M, were significantly different from controls; however, at polymer salt concentrations less than those necessary to balance the cationic charge of MBP, all polymers exhibited a drastic reduction in their ability to inhibit MBP toxicity. These data suggest that the anionic charge of a polyamino acid salt is a critical determinant of its ability to inhibit MBP toxicity.

To better define the point at which polyamino acid salts begin to effectively inhibit MBP toxicity, several of the polymer salts were tested at 2.0, 1.0 and 0.5 times the concentration necessary to balance cationilc charge of MBP at $5 \times 10^{-6}$M. As shown in FIG. 1, all four amino acid polymer salts tested inhibited MBP toxicity to K562 cells at a concentration of 2.0 times the cationic charge of MBP $[2 \times (5 \times 10^{-6}$M$)]$. At a concentration of 1.0 times the cationic charge of MBP, the polyaspartic acid salts partially lost their ability to inhibit MBP whereas the polyglutamic acid salts did not. All of the polymers lost their ability to inhibit MBP at a concentration of 0.5 times the cationic charge of MBP and afforded little protection against MBP. Thus, polyamino acid salts begin to effectively protect K562 cells against MBP toxicity at concentrations between 1.0 to 2.0 times those required to balance the cationic charge of MBP.

Figure 2:
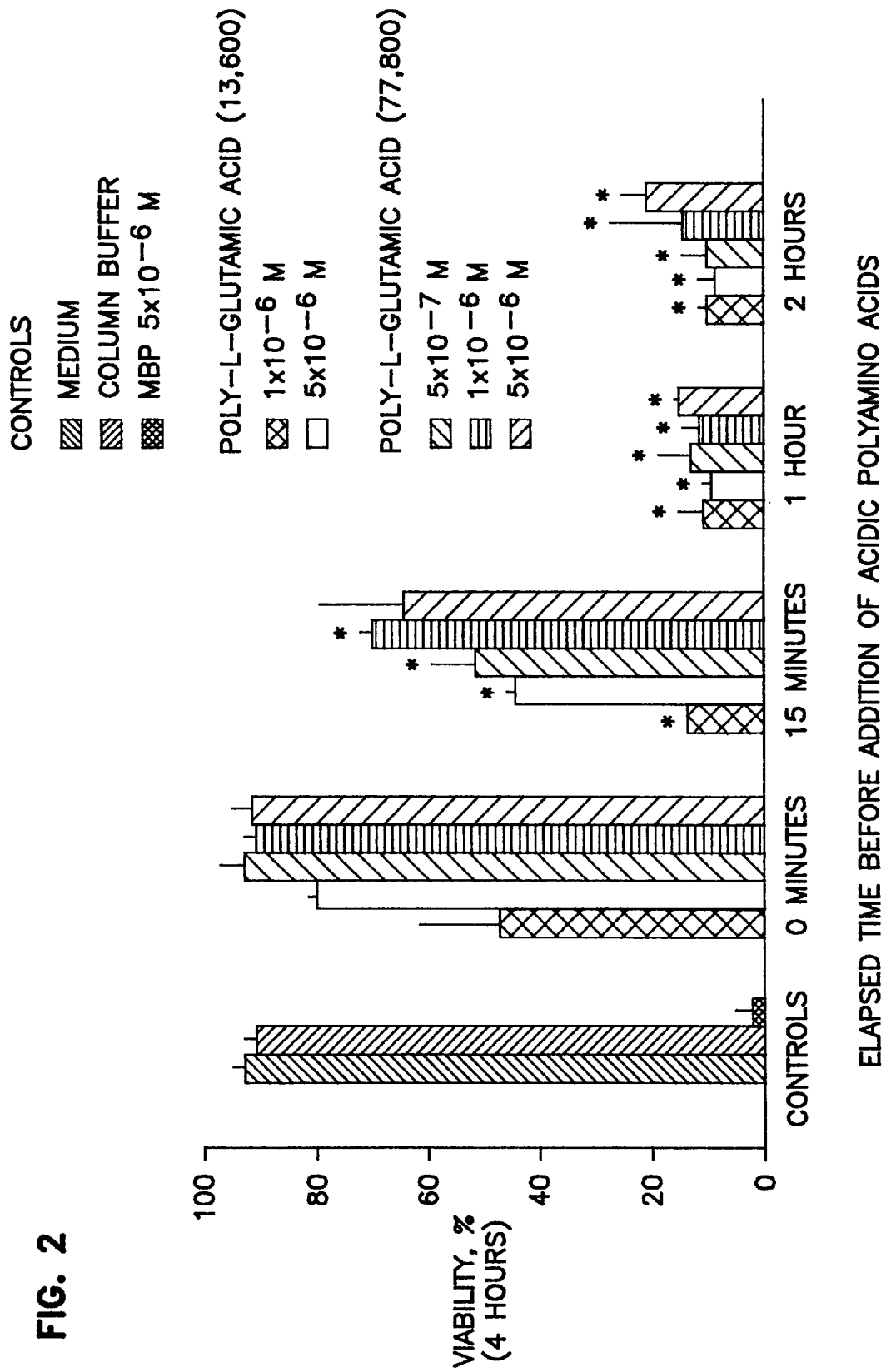
FIG. 2 is a graphic depiction of the acidic polyamino acid salt inhibition of MBP toxicity to K562 cells over time. Acidic polymers were added before MBP (0 minutes) or 15 minutes, 1 hr or 2 hr after addition of MBP to cell cultures. Values are mean percent viability±1SD of 1–2 experiments consisting of duplicate wells. (*) indicates p<0.05 values tested against acidic polyamino acid salt added at 0 minutes using Student's t-test.
Figure 3:
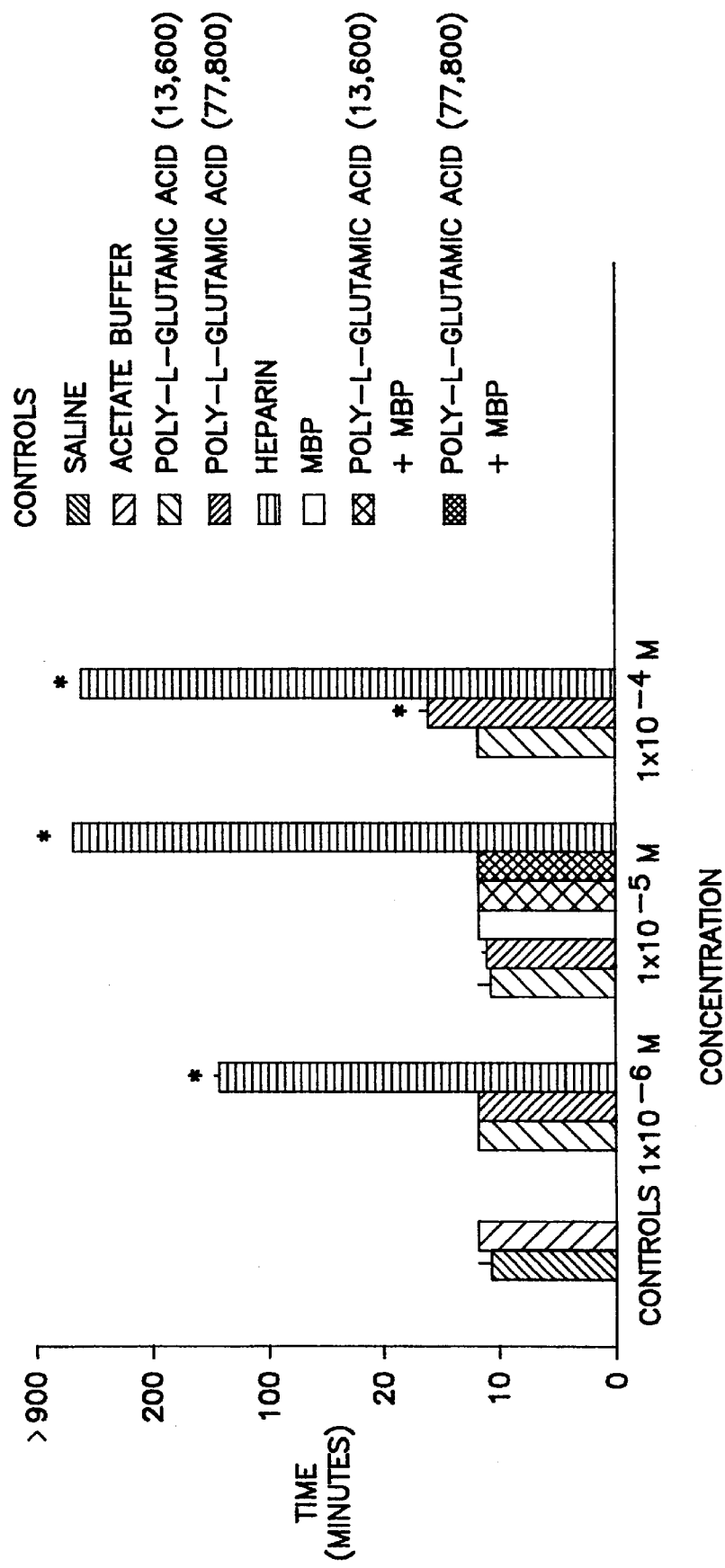
FIG. 3 is a graphic depiction of the effects of acidic polyamino acid salts on blood coagulation. Values are mean coagulation time±1SD of 1–2 experiments in triplicate. (*)

In experiments described above, the polyamino acid salts were added to the K562 cells before addition of MBP. The ability of the polyamino acid salt to inhibit MBP toxicity after MBP had already been added to the cells was also tested. As shown by FIG. 2, concentrations of polyamino acid salts which were effective in inhibiting MBP toxicity when added to cells before MBP were not as effective in inhibiting MBP toxicity when added to the cells after MBP exposure. Some-protection was afforded when the polyamino acid salts were added within 15 minutes after MBP addition, but little protection was seen when the polymers are added one or more hours after MBP addition. Only the sodium salt of poly-L-glutamic acid (77,800 mol wt) at equimolar MBP concentration of $5 \times 10^{-6}$M added 15 minutes after MBP significantly protected against MBP toxicity. Thus, the polyamino acid salts have little effect on K562 viability unless they are added before or very shortly after addition of $5 \times 10^{-6}$M MBP.

2. Inhibition of Poly-L-Arginine and ECP Toxicity to K562 Cells by Acidic Polyamino Acid Salts To determine if this toxic inhibition by polyamino acid salts is limited only to MBP or may apply to other cationic toxins, polyamino acid salts were tested for their ability to inhibit a cationic polyamino acid salt, sodium poly-L-arginine and to inhibit ECP toxicity to K562 cells. Both sodium poly-L-arginine and ECP toxicity were inhibited by acidic polyamino acid salts as shown by the data presented on Table III, below.

TABLE III

Inhibition of ECP and Poly-L-arginine Toxicity by Acidic Polyamino Acid Salts

| | | | Percent Viability of K562 Cells* | | | |
|---|---|---|---|---|---|---|
| | | Controls‡ | Poly-L-arginine or ECP (both at $5 \times 10^{-6}$M) added to acidic poly aa concentrations of | | | |
| | Mol wt | $5 \times 10^{-6}$M | $5 \times 10^{-6}$M | $1 \times 10^{-6}$M | $5 \times 10^{-7}$M | $1 \times 10^{-7}$M |
| Poly-L-glutamic acid** | 13,600 | 96.9 ± 4.5 | <u>99.1 ± 1.3</u>" | $4.9 \times 0.3^{\#}$ | $0.0 \pm 0.0^{\#}$ | $0.0 \pm 0.0^{\#}$ |
| Poly-L-glutamic acid | 77,800 | 97.2 ± 2.5 | 97.9 ± 3.0 | <u>$97.2 \times 4.0$</u> | $22.9 \pm 3.0^{\#}$ | $2.0 \pm 2.9^{\#}$ |
| Poly-L-arginine hydrochloride | 12,000 | 0.0 ± 0.0 | | | | |
| Medium | | 97.8 ± 1.0 | | | | |
| Poly-L-glutamic acid | 13,600 | 100.0 ± 0.0 | $77.2 \pm 4.9^{\#}$ | <u>$73.7 \times 5.8^{\#}$</u> | $50.2 \pm 1.3^{\#}$ | 59.8 ± 20.6 |
| Poly-L-glutamic acid | 77,800 | 100.0 ± 0.0 | 98.3 ± 0.5 | $96.4 \times 5.2$ | <u>91.2 ± 3.3</u> | $58.4 \pm 11.8^{\#}$ |
| ECP | 16,000 | 35.7 ± 6.2 | | | | |
| Medium | | 86.8 ± 2.1 | | | | |

*Values are mean percent viability ± 1 SD of one 4 hr experiment consisting of duplicate wells for poly-L-arginine hydrochloride and a second experiment consisting of duplicate wells for ECP.
‡Controls consist of acidic polyamino acids, poly-L-arginine, ECP or medium tested alone.
"Values underlined are from acidic polyamino acid test concentrations closest to but not less than concentration for balanced charge (Table I) for a particular acidic polyamino acid.
Indicates $p < 0.05$ for values tested against appropriate acidic polyamino acid controls using Student's t-test; poly-L-arginine hydrochloride or ECP added within five minutes after addition of acidic polyamino acid.
**All polyamino acids were used as the sodium salts unless otherwise noted.

Generally, there were no significant differences between test concentrations and controls when polyamino acid test concentrations were at least equal to the concentration needed for a balanced charge for poly-L-arginine•HCl or ECP. Below polyamino acid salt concentrations necessary for a balanced charge, inhibition of toxicity was greatly reduced for all polyamino acid salts tested. Because these polyamino acid salts inhibit poly-L-arginine and ECP toxicity, this mechanism is not specific to MBP and may apply to a wide variety of cationic toxins.

3. Inhibition of MBP Toxicity to Tracheal Ring Epithelium by Polyamino Acid Salts Polyamino acid salts were used as antagonists of MBP toxicity to guinea pig tracheal epithelium as a model for their role as an inhibitor of MBP toxicity in bronchial asthma. The polyglutamic acid salts inhibited MBP toxicity to the tracheal epithelium. Tracheal rings incubated with MBP alone exhibited gross morphologic damage at 24 hr. The damage included ciliostasis and exfoliation of mucosal cells. Precipitates of MBP were apparent on and around the cells. After 48 hr of incubation, only the MBP-alone-treated tracheal rings showed damage. In contrast, the tracheal rings treated with acidic polyglutamic acid salts or a combination of polyglutamic acid salts and MBP appeared normal with actively beating cilia.

4. Inhibition of MBP-Induced Effects on the Airway by Polyglutamic Acid Sodium Salt MBP instillation into the monkeys resulted in an immediate increase in Rrs that peaked between 5 to 10 minutes postinstillation and resolved by 1 hr. Pretreatment with the sodium salt of polyglutamic acid significantly inhibited the MBP-induced increase in Rrs. Polyglutamic acid salt treatment by itself did not alter Rrs (data not shown).

The effects of MBP instillation on airway responsiveness to inhaled methacholine during control and polyglutamic acid salt treatment studies were also tested. MBP administration alone resulted in a dramatic increase in airway responsiveness as indicated by a 10-fold decrease in the calculated dose of methacholine required to cause a 100% increase in Rrs ("the methacholine $PC_{100}$ value"). Polyglutamic acid salt pretreatment significantly inhibited the MBP-induced increase in airway responsiveness in each animal studied.

5. Inhibition of MBP Effects on the Airway by Parenteral Administration of Polyglutamic Acid Sodium Salt As noted above in 4, the effects of MBP on the airways of rhesus monkeys can be blocked by pretreatment with the sodium salt of polyglutamic acid. One could also demonstrate the effectiveness of parenteral administration of polyglutamate by demonstrating its ability to counteract the effect of inhaled MBP on airway responsiveness in monkeys. In this experiment (as in 4 above), MBP will be instilled into the monkeys' airway to cause an immediate increase in Rrs and increased airway responsiveness to inhaled methacholine. Monkeys will be pretreated with the sodium salt of polyglutamic acid to demonstrate that the parenteral administration of polyglutamic acid inhibits the MBP-induced increase in Rrs. To demonstrate the effectiveness of injected polyglutamic acid, 0.1% weight/volume solution of polyglutamic acid sodium salt in phosphate-buffered saline (PBS) will be perfused intravenously at the rate of 20 ml/hr for 2 hours prior to challenge with MBP. The results will show that parenteral infusion with MBP is as effective as topical administration by significantly inhibiting the MBP-induced increases in Rrs and airway responsiveness in the monkeys studied.

6. Effect of Polyamino Acid Salts on Blood Clotting

Although heparin is an effective antagonist of MBP toxicity, its possible clinical use could be limited by its ability to inhibit blood clotting. To determine if polyamino acid salts inhibit blood clotting, whole blood was incubated with heparin or polyglutamic acid salts, and the clotting time was observed. As shown in FIG. 3, at a concentration of $1\times10^{-5}$M, twice the highest polyamino acid salt concentration used in the K562 assays and comparable to that used in the tracheal ring assays, there was no significant difference between polyglutamic acid salts when compared to controls in their ability to inhibit clotting.

The present invention has been exemplified with respect to the neutralization of the toxic effect of MBP on cells, on respiratory epithelium, on causing increases in Rrs and finally on causing bronchial hyperreactivity in monkeys. However, due to the discovery that not only polyglutamic acid salts, but also polyaspartic acid salts, can neutralize the effect of MBP on monkey lung and ECP on tissue culture cells, it is believed that other polyanions can be employed in the present method.

The invention has been described with reference to very specific and preferred embodiments and techniques. However, it should be understood that many variations and modifications may be made while remaining within the spirit and scope of the invention.

What is claimed is:

1. A method for treating an eosinophil-associated hypersensitivity disease selected from the group consisting of bronchial asthma, eosinophil-associated intranasal inflammation, and eosinophil-associated inflammation of the eye comprising administering to a human in need of such treatment an amount of a polymeric polycarboxylic acid or a pharmaceutically acceptable salt thereof having a net negative charge and having a plurality of repeating units of which at least 80 percent of said repeating units contain at least one carboxyl functionality in combination with a pharmaceutically acceptable carrier effective to inhibit or reduce the pathological effects induced by the release of cationic proteins from eosinophils.

2. The method of claim 1 wherein at least 90 percent of said repeating units contain at least one carboxyl functionality.

3. The method of claim 2 wherein at least 95 percent of said repeating units contain at least one carboxyl functionality.

4. The method of claim 1 wherein said polymeric polycarboxylic acid salt is a polyamino acid salt.

5. The method of claim 1 wherein said repeating unit is provided by a monomer selected from the group consisting of acrylic acid, methacrylic acid, fumaric acid, maleic acid, maleic anhydride, itaconic acid and crotonic acid.

6. The method of claim 5 wherein said repeating unit is provided by a monomer selected from the group consisting of acrylic acid, methacrylic acid and maleic acid.

7. The method of claims 1 or 5 wherein said polycarboxylic acid has a molecular weight of about 10,000–100,000.

8. The method of claim 1 wherein the polycarboxylic acid further comprises from about 0.05 to about 1.5 percent cross-linking agent.

9. The method of claim 8 wherein the cross-linking agent is selected from the group consisting of divinylether, divinylbenzene, N,N-diallyacrylamide, 3,4-dihydroxy-1,5-hexadiene, 2,5-dimethyl-1,5-hexadiene and a polyalkenyl polyether.

10. The method of claim 1 wherein the polycarboxylic acid or pharmaceutically acceptable salt thereof is administered parenterally to said human in combination with a pharmaceutically acceptable liquid carrier.

11. The method of claim 10 wherein the polycarboxylic acid or pharmaceutically acceptable salt thereof is administered by injection.

12. The method of claim 10 wherein the polycarboxylic acid or pharmaceutically acceptable salt thereof is administered by infusion.

13. The method of claim 10 wherein the polycarboxylic acid or pharmaceutically acceptable salt thereof is administered topically.

14. The method of claim 13 wherein the polycarboxylic acid or pharmaceutically acceptable salt thereof is administered transdermally.

15. The method of claim 10 wherein the polycarboxylic acid or pharmaceutically acceptable salt thereof is administered by inhalation or insufflation.

16. The method of claim 1 wherein the polycarboxylic acid or pharmaceutically acceptable salt thereof is administered enterally, in combination with a pharmaceutically acceptable carrier.

17. The method of claims 1, 10 or 16 wherein the carrier is an isotonic aqueous carrier.

18. The method of claim 1 wherein the eosinophil-associated hypersensitivity disease is bronchial asthma, eosinophil-associated intranasal inflammation, or eosinophil-associated inflammation of the eye.

19. The method of claim 18 wherein the hypersensitivity disease is bronchial asthma.

* * * * *